United States Patent
Javitt et al.

(10) Patent No.: US 10,165,965 B1
(45) Date of Patent: Jan. 1, 2019

(54) NONINVASIVE METHOD FOR MEASURING LACTIC ACID AND DETECTION OF ANAEROBIC EXERCISE FOR EVALUATING FITNESS

(71) Applicant: Roy Pinchot, Silver Spring, MD (US)

(72) Inventors: Norman B. Javitt, New York, NY (US); Roy Pinchot, Silver Spring, MD (US)

(73) Assignee: Roy Pinchot, Silver Spring, MD (US)

( * ) Notice: Subject to any disclaimer, the term of this patent is extended or adjusted under 35 U.S.C. 154(b) by 148 days.

(21) Appl. No.: 15/331,293

(22) Filed: Oct. 21, 2016

Related U.S. Application Data

(60) Provisional application No. 62/285,204, filed on Oct. 22, 2015.

(51) Int. Cl.
*A61B 5/08* (2006.01)
*A61B 5/22* (2006.01)

(52) U.S. Cl.
CPC .............. *A61B 5/082* (2013.01); *A61B 5/222* (2013.01)

(58) Field of Classification Search
CPC ................................. A61B 5/082; A61B 5/222
See application file for complete search history.

(56) References Cited

U.S. PATENT DOCUMENTS

| | | | |
|---|---|---|---|
| 6,899,706 B2 | 5/2005 | Slatkine | |
| 8,512,676 B1 | 8/2013 | Eghbalnia et al. | |
| 8,920,334 B2 | 12/2014 | Stockmann et al. | |
| 9,278,145 B2 | 3/2016 | Stockmann et al. | |
| 2015/0196248 A1* | 7/2015 | Cook | A61B 5/486 600/531 |

FOREIGN PATENT DOCUMENTS

DE   19731889 A1 *  1/1999   ......... G01N 21/3504

OTHER PUBLICATIONS

Péronnet, et al. "Respective oxidation of 13C-labeled lactate and glucose ingested simultaneously during exercise." J Appl Physiol (1985). Feb. 1997;82(2):440-6.*

Coggan, et al. "Isotopic estimation of CO2 production during exercise before and after endurance training." J Appl Physiol (1985). Jul. 1993;75(1):70-5.*

(Continued)

*Primary Examiner* — Navin Natnithithadha
*Assistant Examiner* — Eric J Messersmith
(74) *Attorney, Agent, or Firm* — Panitch Schwarze Belisario & Nadel LLP

(57) ABSTRACT

A method of determining when a subject is experiencing anaerobic exercise during an exercise session, for determining effectiveness of a training period, and/or for determining a level of lactic acid produced by a subject during an exercise session may involve the administration of a bicarbonate comprising a carbon-13 isotope. Expired air may be monitored, and a ratio of carbon dioxide comprised of the carbon-13 isotope and carbon dioxide comprised of a carbon-12 isotope may be determined at one or more points in time. Charts of the ratios may be used to indicate onset of anaerobic exercise or effectiveness of a training period, and/or the determined ratio(s) may be used to indicate lactic acid production.

14 Claims, 2 Drawing Sheets

(56) References Cited

OTHER PUBLICATIONS

Barstow, et al. "Changes in breath 13CO2/12CO2 consequent to exercise and hypoxia." J Appl Physiol (1985). Feb. 1989;66(2):936-42.*
Machine Translation of DE 19731889 A1.*
McCue et al., "13 C-Breath testing in animals: theory, applications, and future directions," J. Comp. Physiol B, vol. 186, pp. 265-285 (2016).
Myers et al., "Dangerous Curves* A Perspective on Exercise, Lactate, and the Anaerobic Threshold," Chest, vol. 111, pp. 787-795 (1997).
Speakman et al., "Validation of the labeled bicarbonate technique for measurement of short-term energy expenditure in the mouse," Zeitschrift fur Ernahrungswissenschaft, vol. 36, pp. 273-277 (1997).
Romijn et al., "Comparison of indirect calorimetry and a new breath 12C/13C ratio method during strenuous exercise," American Journal of Physiology, pp. 64-71 (Aug. 1992).
Kisaka et al., "CO2 pulse and acid-base status during increasing work rate exercise in health and disease," Respiratory Physiology & Neurobiology, vol. 218, pp. 46-56 (2015).

* cited by examiner

NONINVASIVE METHOD FOR MEASURING LACTIC ACID AND DETECTION OF ANAEROBIC EXERCISE FOR EVALUATING FITNESS

CROSS-REFERENCE TO RELATED APPLICATIONS

This application claims priority from U.S. Provisional Patent Application No. 62/285,204, filed Oct. 22, 2015, the disclosure of which is hereby incorporated by reference herein in its entirety.

FIELD OF ENDEAVOR

Various aspects of this disclosure may generally relate to noninvasive methods to evaluate fitness due to exercise and/or training in a subject. The methods disclosed herein can be used to alter exercise sessions and/or training periods to produce optimal results for the subject, e.g., an increased level of overall fitness.

BACKGROUND

The intense interest in sports, exercise and fitness training has produced a vast literature that describes all the events that occur during an individual's period of exercise. Not all the studies are in agreement, but basic changes that occur in all individuals have been established by a variety of techniques including the direct biopsy of muscle tissue and blood sample analysis. Oxygen consumption and $CO_2$ production are fundamental quantities both at rest and during exercise. However, these parameters are difficult and inconvenient to ascertain during exercise. Therefore, reliable, easy to measure surrogate parameters are needed.

If energy production by muscles during exercise kept pace with energy demand, then the complete oxidation of glucose and fatty acids as the major sources for energy would continue. However, it was found in early studies that during intense exercise there is a progressive increase in lactic acid in muscles, some of which is transported into plasma. This build-up in lactic acid, often referred to as anaerobic metabolism or glycolysis, represents an imbalance between energy demand and energy supply that may be restored by completing its oxidation at a later time.

A comprehensive review discusses whether lactic acid production during exercise should be viewed as a continuous function or a threshold, based on the interpretation of mathematical models (Myers and Ashley, Chest 111:787-95 (1997)). Nevertheless, it is clear from plasma lactate analysis that sharp inflection points do occur in the later phases of maximum exercise.

Radioactive and/or stable isotopes of sodium bicarbonate have been used previously for evaluating exercise performance (Speakman and Thomson, Zeitschrift fur Ernahrungswissenschaft 36:273-7 (1997)); however, the use of the isotopes of sodium bicarbonate did not permit a clear distinction between $CO_2$ production attributable to buffering and $CO_2$ produced that related only to energy production. Therefore, it was not possible to distinguish between aerobic and anaerobic metabolism during exercise and during the post-exercise period. As such, methods are needed to distinguish between the $CO_2$ produced because of lactate production from that generated by complete oxidation, which, in turn, would allow monitoring of the proportion of aerobic and anaerobic metabolism during exercise.

BRIEF SUMMARY OF ASPECTS OF THE DISCLOSURE

Various aspects of the disclosure may relate to methods for determining when a subject is experiencing anaerobic exercise during an exercise session. The methods may comprise: a) administering to a subject a bicarbonate salt, which may be sodium bicarbonate ($NaHCO_3$), comprising a carbon-13 isotope prior to the exercise session; b) monitoring expired air from the subject during the exercise session; c) measuring a ratio of carbon dioxide comprising the carbon-13 isotope ($^{13}CO_2$) to carbon dioxide comprising a carbon-12 isotope ($^{12}CO_2$) in the monitored expired air; d) charting or otherwise recording/monitoring the $^{13}CO_2$ to $^{12}CO_2$ ratio during the exercise session; e) determining an inflection point in the $^{13}CO_2$ to $^{12}CO_2$ ratio, wherein an increase in the $^{13}CO_2$ to $^{12}CO_2$ ratio after the inflection point indicates that the subject is experiencing anaerobic exercise during the exercise session.

Further aspects of the disclosure may relate to methods for determining the effectiveness of a training period in a subject. The methods may comprise: a) administering to a subject a bicarbonate salt, which may be sodium bicarbonate, comprising a carbon-13 isotope prior to an exercise session; b) monitoring expired air from the subject during the exercise session; c) measuring a ratio of carbon dioxide comprising the carbon-13 isotope ($^{13}CO_2$) to carbon dioxide comprising a carbon-12 isotope ($^{12}CO_2$) in the monitored expired air; d) charting or otherwise monitoring/recording the $^{13}CO_2$ to $^{12}CO_2$ ratio during the exercise session; e) determining an inflection point in the $^{13}CO_2$ to $^{12}CO_2$ ratio, wherein an increase in the $^{13}CO_2$ to $^{12}CO_2$ ratio after the inflection point indicates that the subject is experiencing anaerobic exercise during the exercise session; f) repeating steps (a)-(e) for at least two exercise sessions as part of a training period; and g) comparing results of each exercise session for the training period, wherein an increase in an amount of time for the inflection point indicating anaerobic exercise over the course of the training period indicates that the training period is effective.

Further aspects of the disclosure may relate to methods for determining a level of production of lactic acid in a subject during an exercise session. The methods may comprise: a) administering to a subject a sodium bicarbonate comprising a carbon-13 isotope prior to the exercise session; b) monitoring expired air from the subject during the exercise session; c) measuring a ratio of carbon dioxide comprising the carbon-13 isotope ($^{13}CO_2$) to carbon dioxide comprising a carbon-12 isotope ($^{12}CO_2$) in the monitored expired air; and d) utilizing this ratio as a surrogate for lactic acid, calculating a level of production of lactic acid based on the measured $^{13}CO_2$ to $^{12}CO_2$ ratio in the expired air.

In certain aspects of the disclosure, the subject the sodium bicarbonate comprising the carbon-13 isotope may be administered to the subject at a time significantly prior to the exercise session, e.g., at least two to four hours prior to the exercise session. Optionally, the expired air prior to the exercise session may be monitored, and the $^{13}CO_2$ to $^{12}CO_2$ ratio in the monitored expired air may be measured and monitored.

In certain aspects of the disclosure, monitoring the expired air from the subject comprises the subject breathing into a device capable of measuring the $^{13}CO_2$ to $^{12}CO_2$ ratio in the expired air. Optionally, the device may further comprise a processing program and a user interface and may automatically perform the measurements/monitoring/calculations.

Other aspects, features and advantages will be apparent from the following disclosure, including the detailed description of various aspects of this disclosure and the appended claims.

BRIEF DESCRIPTION OF THE DRAWINGS

The foregoing summary, as well as the following detailed description, will be better understood when read in conjunction with the appended drawings, in which.

DETAILED DESCRIPTION OF VARIOUS ASPECTS OF THE DISCLOSURE

Figure 1:
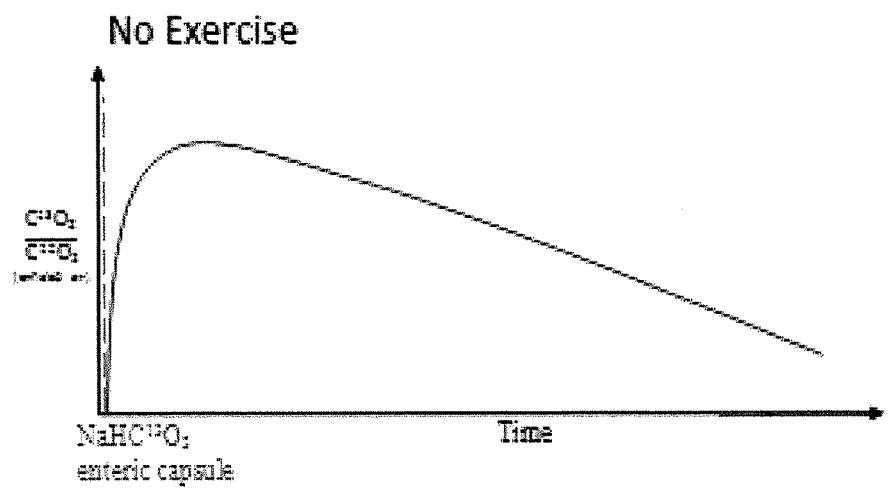
FIG. 1 is a graph of the ratio of $^{13}CO_2/^{12}CO_2$ over time in a subject that has not exercised.

Unless defined otherwise, all technical and scientific terms used herein have the same meaning as commonly understood to one of ordinary skill in the art to which this invention pertains. Otherwise, certain terms used herein have the meanings as set forth herein. All patents, published patent applications and publications cited herein are incorporated by reference as if set forth fully herein. It must be noted that as used herein and in the appended claims, the singular forms "a," "an," and "the" include plural reference unless the context clearly dictates otherwise.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit set forth herein.

As used herein, the term "subject" means any animal, preferably a mammal, most preferably a human.

As used herein the term "exercise session" refers to any type of exercise for any amount of time. Exercise may include, but is not limited to, one or more of walking, jogging, running, basketball, football, baseball, hockey, tennis, soccer, swimming, track and field, field hockey, lacrosse, golf, racing, boxing, kickboxing, mixed martial arts, martial arts, wrestling, bicycling, and cricket. An exercise session can include a practice session for a particular sport, or, alternatively, it can include a game for the particular sport. An exercise session can be any amount of time; for example, an exercise session can be at least 10 seconds, at least 1 minute, at least 5 minutes, at least 10 minutes, at least 30 minutes, at least 1 hour, at least 2 hours, at least 3 hours, at least 5 hours, at least 10 hours, or at least 20 hours.

As used herein the term "training period" refers to at least two or more exercise sessions of the same nature, e.g., two or more basketball practices, two or more swimming practices, two or more hockey practices. A training period can, for example, refer to multiple exercise sessions over a determined time period. By way of an example, a training period can refer to multiple exercise sessions over the course of a season for a particular sport. Alternatively, the training period can refer to multiple exercise sessions over the course of the offseason for a particular sport.

As used herein the term "effectiveness of a training period" refers to whether the subject has gained any advantage from the training period. If the subject has gained an advantage (e.g., the subject has greater endurance or more energy during an exercise session), then the training session has been effective. If the subject has not gained an advantage (e.g., the subject has less or the same endurance as determined by when onset of anaerobic exercise occurs during the exercise session or less energy during the exercise session), then the training period has not been effective.

It is generally accepted that fitness in performance of a task may improve with training, which in terms of energy metabolism may be indicated by an increase in the proportion of aerobic metabolism and a decrease in the proportion of anaerobic metabolism, which may be indicated by a decrease in lactate production.

During exercise, at a certain point the continuous rise in lactic acid in the muscles may begin to inhibit the performance of the athlete, and the result may be increasing fatigue and declining performance. Measuring the level of lactic acid during exercise may be helpful to maximize the effectiveness of athletic training and the intelligent use of effort and rest. Thus, various techniques provided herein may relate to noninvasive methods for determining the level of lactic acid produced during exercise in a subject in real time, such that determining the levels of lactic acid produced while exercising can lead to changes in training regimens to increase the overall fitness of the subject. By distinguishing between the $CO_2$ production that occurs during exercise as a result of lactate buffering from the $CO_2$ that results from energy production utilizing the methods disclosed herein, work performance with regard to the proportion of aerobic and anaerobic metabolism that is necessary to provide energy can be evaluated.

One general aspect of this disclosure may relate to methods for determining when a subject is experiencing anaerobic exercise during an exercise session. Such methods may include: a) administering to a subject a bicarbonate salt, which may be sodium bicarbonate ($NaHCO_3$), comprising a carbon-13 isotope prior to the exercise session; b) monitoring expired air from the subject during the exercise session; c) measuring a ratio of carbon dioxide comprising the carbon-13 isotope ($^{13}CO_2$) to carbon dioxide comprising a carbon-12 isotope ($^{12}CO_2$) in the monitored expired air over a plurality of time instants during the exercise session; d) charting, or otherwise recording, the $^{13}CO_2$ to $^{12}CO_2$ ratio during the exercise session; and e) determining an inflection point in the $^{13}CO_2$ to $^{12}CO_2$ ratio, wherein an increase in the $^{13}CO_2$ to $^{12}CO_2$ ratio after the inflection point may indicate that the subject is experiencing anaerobic exercise during the exercise session. Note that "charting" may be understood to refer to any type of useful visual rendering of the relevant data, for example, but not limited to, a data plot (e.g. versus time), listing, etc. In d), charting or recording of the $^{13}CO_2$ to $^{12}CO_2$ ratio may be done in an automated fashion, by a device used to perform the measurements of the ratio or by a separate computing device coupled to the measurement device or otherwise receiving data from the measurement device and programmed to perform store and/or chart or plot the measurement of the $^{13}CO_2$ to $^{12}CO_2$ ratio. The measurement device or computing device may further be enabled to determine the inflection point.

Determining when a subject is experiencing anaerobic exercise during an exercise session can be valuable for the subject. Utilizing this information can, for example, lead a subject (or someone supervising the subject; it should be understood that, although the "subject" is referred to below as making observations, adjustments, etc., based on the information obtained, this is intended to also refer to someone working with the subject, such as an athletic trainer, physical therapist, doctor, etc.) to better design exercise sessions to improve the subject's overall fitness and help delay the onset of lactic acid accumulation due to anaerobic conditions. The subject can, for example, correlate the specific activity of the exercise session to the onset of the anaerobic portion of the exercise and design the exercise session to reach the anaerobic portion of the exercise session later in the session. Alternatively, the subject can design the exercise session to reach the anaerobic portion of the exercise session earlier in the session. The subject may be able to design each session based on a desired outcome of the session. In this way, the subject may reach the maximum fitness effect of the exercise session in whatever time is available and may be able to change the ratio of level of effort, duration of effort, and/or rest intervals to emphasize or improve different aspects of the training effect (i.e. heart/lung fitness, muscle strength, rapidity of recovery, technique improvement, etc.) and/or create workout variety to maintain high motivation and interest.

A further aspect of this disclosure may relate to methods for determining the effectiveness of a training period for a subject. Such methods may include: a) administering to a subject a bicarbonate salt, which may be sodium bicarbonate, comprising a carbon-13 isotope prior to an exercise session; b) monitoring expired air from the subject during the exercise session; c) measuring a ratio of carbon dioxide comprising the carbon-13 isotope ($^{13}CO_2$) to carbon dioxide comprising a carbon-12 isotope ($^{12}CO_2$) in the monitored expired air at a plurality of time instants over the exercise session; d) charting, or otherwise recording, the $^{13}CO_2$ to $^{12}CO_2$ ratio during the exercise session; e) determining an inflection point in the $^{13}CO_2$ to $^{12}CO_2$ ratio, wherein an increase in the $^{13}CO_2$ to $^{12}CO_2$ ratio after the inflection point indicates that the subject is experiencing anaerobic exercise during the exercise session; f) repeating steps (a)-(e) for at least two exercise sessions as part of a training period; and g) comparing the charted or otherwise recorded results of each exercise session for the training period, wherein an increase in an amount of time for the inflection point indicating anaerobic exercise over the course of the training period may indicate that the training period is effective. Again, charting or recording of the $^{13}CO_2$ to $^{12}CO_2$ ratio may be done in an automated fashion, by a device used to perform the measurements of the ratio or by a separate computing device coupled to the measurement device or otherwise receiving data from the measurement device and programmed to perform store and/or chart or plot the measurement of the $^{13}CO_2$ to $^{12}CO_2$ ratio. The measurement device or computing device may further be enabled to determine the inflection point.

Determining an effectiveness of a training period for a subject may be extremely valuable for the subject. Utilizing the methods disclosed herein, it may be determined if the subject's overall training period is increasing the subject's endurance, and thus, delaying the onset of anaerobic exercise during each exercise session. By comparing each exercise session utilizing the methods disclosed herein, a subject may tailor an exercise session to achieve a desired result. By being able to achieve a desired result for each exercise session, a subject may improve overall fitness level during the training period.

Further aspects of this disclosure may relate to methods for determining a level of production of lactic acid in a subject during a test, which may be an exercise session or may be some medical test (e.g., lactic acid build-up during a medical event or procedure may, in some situations, indicate a serious body response that may be fatal). Such methods may comprise: a) administering to a subject a bicarbonate salt, which may be sodium bicarbonate, comprising a carbon-13 isotope prior to the test; b) monitoring expired air from the subject during the test; c) measuring a ratio of carbon dioxide comprising the carbon-13 isotope ($^{13}CO_2$) to carbon dioxide comprising a carbon-12 isotope ($^{12}CO_2$) in the monitored expired air; and d) utilizing the ratio of $^{13}CO_2$ to $^{12}CO_2$ as a surrogate to estimate a level of production of lactic acid being produced by the subject at the time of the test.

By administering to the subject sodium bicarbonate comprising the carbon-13 isotope prior to testing, the equilibration with the endogenous bicarbonate pools comprising a carbon-12 isotope in the subject may be enabled. By equilibrating the carbon-13 and carbon-12 isotopes prior to testing, the $CO_2$ production that occurs as a result of lactate buffering may be distinguished from the $CO_2$ that may result from normal (non-exercise/aerobic exercise) energy production. Consequently, the ratio of $^{13}CO_2$ to $^{12}CO_2$ may indicate a level of lactic acid production due to "abnormal" (or anaerobic) activity in the body and may be used to estimate a quantity of lactic acid, at least a relative quantity thereof, produced as a result of lactate buffering. This may be based on known relationships between lactic acid production and $CO_2$ production.

According to a further aspect of this disclosure, the sodium bicarbonate comprising the carbon-13 isotope may be administered to the subject prior to the exercise session, e.g., but not limited to, at least three to four hours prior to the exercise session. Optionally, the expired air prior to the exercise session may be monitored, and the $^{13}CO_2$ to $^{12}CO_2$ ratio in the monitored expired air may be measured and charted, or otherwise monitored, to determine when the carbon-13 and carbon-12 isotopes are equilibrated. The resulting information may be used, e.g., to provide a baseline measurement for comparison with future tests (e.g., during exercise sessions).

According to another aspect of this disclosure, monitoring the expired air from the subject may include the subject breathing into a device capable of measuring the $^{13}CO_2$ to $^{12}CO_2$ ratio in the expired air. Devices for measuring the $^{13}CO_2$ to $^{12}CO_2$ ratio in the expired air are known in the art, see, e.g., isotope ratio mass spectrometer systems (IRMS), vapor-phase isotope analyzer (Picarro, Inc.; Sunnyvale, Calif.), PCONE/Breathtek instruments (Otsuka Pharmaceutical, Inc., Rockville, Md. & Japan), and Gas Analyzing Thermopile Detection instruments (Dexter Research, Dexter, Mich.). Other devices may also currently exist. Optionally, the device may further comprise a processing program and a user interface. The processing program may, for example, chart/monitor the $^{13}CO_2$ to $^{12}CO_2$ ratio in the expired air over time at each time point in which the $^{13}CO_2$ to $^{12}CO_2$ ratio in the expired air was measured. The processing program may, for example, be designed to be utilized on any computing system, e.g., a tablet, a cellular phone, a desktop computer. The processing system may comprise a user interface that may enable manipulation of the data collected. By way of a non-limiting example, if an exercise session is three hours long, the user interface could be utilized to review the charted $^{13}CO_2$ to $^{12}CO_2$ ratio in the expired air over the first hour of the exercise session. By way of another non-limiting example, if the data collected is being utilized to determine the effectiveness of a training period, the user interface of the processing system may be utilized to overlay charted data for multiple exercise sessions to determine whether the training period is effective, i.e., whether there is a delay in the onset of anaerobic exercise during an exercise period.

Various aspects of this disclosure may be better understood by reference to the non-limiting examples that follow, but those skilled in the art will readily appreciate that the examples are only illustrative of various aspects of what is more fully described in the accompanying claims.

EXAMPLES

Example 1: No Exercise

In this first example, enteric-coated $NaH^{13}CO_3$ may be administered orally, e.g., 4 hours prior to exercise performance. A rapid increase in the $^{13}CO_2/^{12}CO_2$ ratio in expired air may typically occur, as the bicarbonate is absorbed from the small intestine. In accordance with the Henderson-Hasselbalch equation, a proportion of the absorbed $NaH^{13}CO_3$ is converted to $^{13}CO_2$. By four hours (or less), intestinal absorption is substantially complete, and sampling of expired air may indicate equilibration with maximum plateau values of the $^{13}CO_2/^{12}CO_2$ ratios. Without exercise, normal whole-body metabolism may continually generate $^{12}CO_2$ with a progressive fall in the $^{13}CO_2/^{12}CO_2$ ratio in expired air during the day (FIG. 1).

Example 2: Anaerobic Exercise

When an individual increases activity beyond the capacity for the muscles to continue complete oxidation, lactic acid may begin to accumulate in the muscles and to enter into plasma. The rise in lactic acid in plasma may be recognized as an indicator of anaerobic metabolism.

Figure 2:
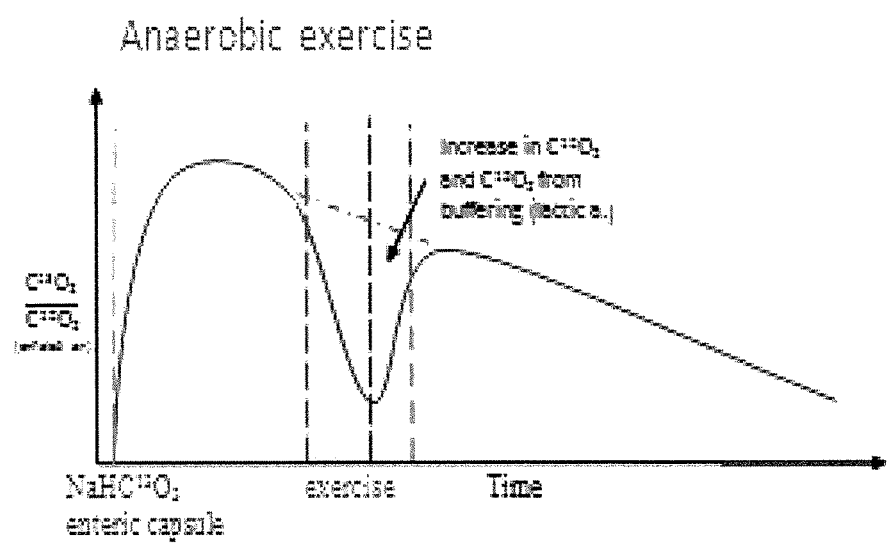
FIG. 2 is a graph of the ratio of $^{13}CO_2/^{12}CO_2$ over time in a subject that has undergone anaerobic exercise.

Lactic acid has a pH much lower than plasma pH and must be buffered immediately by body stores of sodium bicarbonate. Because the body stores of bicarbonate now contain both $NaH^{13}CO_3$ and $NaH^{12}CO_3$, as a result of prior administration of sodium bicarbonate, both will be released into plasma and into expired air as $^{13}CO_2$ and $^{12}CO_2$. Thus, the amount of $^{13}CO_2$ in expired air will increase and will be indicated by a rise in the $^{13}CO_2/^{12}CO_2$ ratio (FIG. 2). This marks the beginning of lactic acid accumulation, which is the hallmark of anaerobic exercise.

After cessation of exercise, lactic acid production may return to basal levels with a decrease in the amount of $^{13}CO_2$ that is generated and a progressive lowering of the $^{13}CO_2/^{12}CO_2$ ratio (FIG. 2).

Example 3: Evaluation of Fitness

Figure 3:
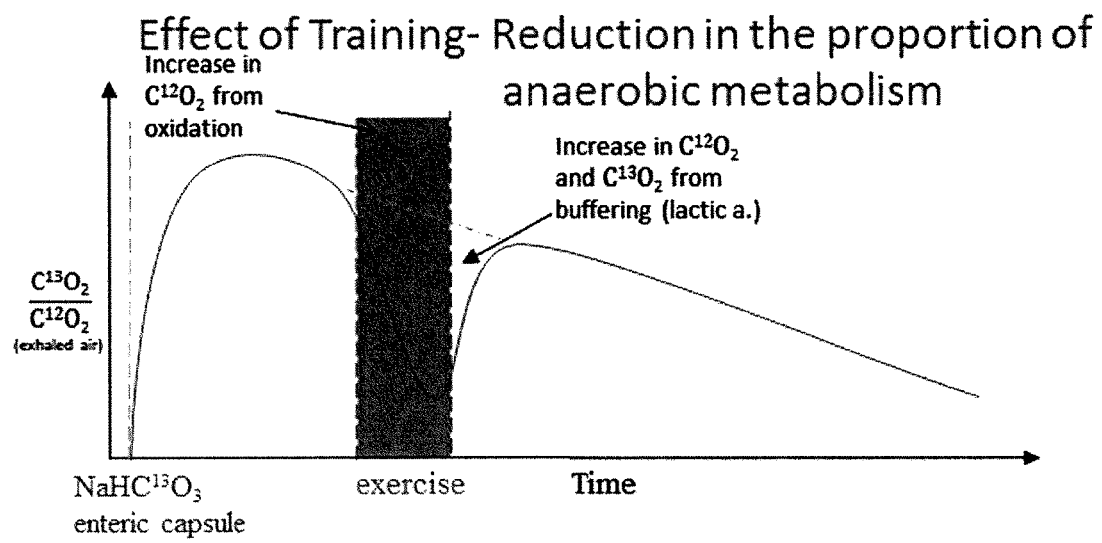
FIG. 3 is a graph of the ratio of $^{13}CO_2/^{12}CO_2$ over time in a subject demonstrating the effects of training.

The noninvasive detection of anaerobic exercise may be applicable to the determination of fitness for performance of a task. At the beginning of training for performing a specific task, as may occur, e.g., in competitive track or swimming events, etc., the novice may enter the anaerobic phase of exercise at a relatively early time frame relative to the exercise period. Monitoring $^{13}CO_2/^{12}CO_2$ ratios in expired air at intervals from the beginning of exercise to the end of the exercise period may be used to indicate the time when anaerobic metabolism (lactic acid production) began and when the positive effects of aerobic training were diminished. (FIG. 3).

With training, the need for anaerobic metabolism for generating energy may typically diminish, beginning at a relatively later time frame, signaled by a reduction in the $^{13}CO_2$ output attributable to a later onset of lactic acid buffering.

Thus, during training, each individual may serve as his or her own control. By comparing the records obtained at the beginning of a training period to those later, when performance has improved, a fitness/exercise regimen pattern may emerge.

Example 4: Evaluating Game Status

Another example application of the techniques disclosed herein is to evaluate the status of athletes during a game, such as, but not limited to basketball, football, soccer or baseball, to maximize their performance potential. In this application, the individual's performance may be monitored during practice sessions providing expired air $^{13}CO_2/^{12}CO_2$ records. $NaH^{13}CO_3$ may taken, e.g., with a meal, prior to the game. A sample of expired air may be taken just prior to the warm-up period and after the warm-up period. Expired air samples taken during the game and rest period, when compared to previous records of the individual, may indicate the individual's current level of fatigue with regard to anaerobic metabolism and ability to continue play at a high level of performance—or the individual's need for rest to return to maximum performance. Later testing may be used to indicate that the individual has recovered and is ready to again deliver a high level of performance.

Example 5: Effect on Rehabilitation Patient

Another example application of the techniques disclosed herein is to utilize this method to maximize the effect of exercise in the rehabilitation of medical patients where exercise and fitness are prescribed as therapy to assist in ameliorating conditions resulting from, for example, cardiac events, diabetes, or other medical conditions for which a regimen of exercise and fitness may be beneficial for rehabilitation. Enteric-coated $NaH^{13}CO_3$ may be administered orally prior to exercise performance. The noninvasive detection of anaerobic exercise may be applicable to maximize the effect of an exercise/fitness regimen and determination of a patient's fitness levels for the purpose of rehabilitation. At the beginning of exercise, the patient may enter the anaerobic phase of exercise at a relatively early time frame relative to the exercise period. Monitoring $^{13}CO_2/^{12}CO_2$ ratios in expired air at intervals from the beginning of exercise to the end of the exercise period may be used to indicate the time when anaerobic metabolism (lactic acid production) began and the positive effects of aerobic exercise were diminished. (FIG. 3). With training, the need for anaerobic metabolism for generating energy may typically diminish, beginning at a relatively later time frame, signaled by a reduction in the $^{13}CO_2$ output, attributable to a later onset of lactic acid buffering and a positive effect toward rehabilitation through exercise. Thus, during training, each individual undergoing exercise rehabilitation may serve as his or her own control or have monitoring performed by a fitness or rehabilitation center. By comparing the records obtained at the beginning of a exercise period to those later, when performance has improved, a fitness/exercise regimen pattern may emerge.

It will be appreciated by those skilled in the art that changes could be made to the above without departing from the broad inventive concept thereof. It is understood, therefore, that this invention is not limited to the particular aspects disclosed herein, but it is intended to cover modifications within the spirit and scope of the present disclosure, including the accompanying claims.

What is claimed is:

1. A method for determining when a subject is experiencing anaerobic exercise during an exercise session and for modifying a subsequent exercise session, the method comprising:
 a. administering to the subject a bicarbonate salt comprising a carbon-13 isotope prior to the exercise session;
 b. monitoring expired air from the subject during the exercise session;
 c. measuring a ratio of carbon dioxide comprising the carbon-13 isotope ($^{13}CO_2$) to carbon dioxide comprising a carbon-12 isotope ($^{12}CO_2$) in the monitored expired air at a plurality of time instants, to obtain a plurality of ratio measurements over a period of the exercise session;
 d. recording the plurality of ratio measurements; and
 e. determining an inflection point in the $^{13}CO_2$ to $^{12}CO_2$ ratio measurements, wherein an increase in the $^{13}CO_2$ to $^{12}CO_2$ ratio after the inflection point indicates that the subject is experiencing anaerobic exercise during the exercise session; and
 f. modifying a subsequent exercise session, relative to the exercise session, based on the indication of anaerobic exercise.

2. The method of claim 1, further comprising monitoring expired air prior to the exercise session and measuring and recording the $^{13}CO_2$ to $^{12}CO_2$ ratio in the monitored expired air.

3. The method of claim 1, wherein monitoring the expired air from the subject comprises having the subject breathe into a device capable of measuring the $^{13}CO_2$ to $^{12}CO_2$ ratio in the expired air.

4. The method of claim 3, wherein at least the measuring and recording are performed by the device.

5. The method of claim 1, wherein the recording comprises charting the plurality of ratio measurements.

6. The method of claim 1, wherein the bicarbonate salt is sodium bicarbonate ($NaHCO_3$).

7. A method for determining the effectiveness of a training period in a subject, the method comprising:
 a. administering to a subject a bicarbonate salt comprising a carbon-13 isotope prior to an exercise session;
 b. monitoring expired air from the subject during the exercise session;
 c. measuring a ratio of carbon dioxide comprising the carbon-13 isotope ($^{13}CO_2$) to carbon dioxide comprising a carbon-12 isotope ($^{12}CO_2$) in the monitored expired air at a plurality of time instants, to obtain a plurality of ratio measurements over a period of the exercise session;
 d. recording the plurality of ratio measurements;
 e. determining an inflection point in the plurality of ratio measurements, wherein an increase in the $^{13}CO_2$ to $^{12}CO_2$ ratio after the inflection point indicates that the subject is experiencing anaerobic exercise during the exercise session;
 f. repeating steps (a)-(e) for at least two exercise sessions as part of a training period; and
 g. comparing at least the inflection points associated with the at least two exercise sessions of the training period, wherein an increase in an occurrence time for the inflection point over the course of the training period indicates that the training period is effective, and wherein a decrease in the occurrence time for the inflection point over the course of the training period indicates that the training period is ineffective.

8. The method of claim 7, further comprising monitoring expired air prior to the exercise session and measuring and recording the $^{13}CO_2$ to $^{12}CO_2$ ratio in the monitored expired air.

9. The method of claim 7, wherein monitoring the expired air from the subject comprises having the subject breathe into a device capable of measuring the $^{13}CO_2$ to $^{12}CO_2$ ratio in the expired air.

10. The method of claim 9, wherein at least the measuring and recording are performed by the device.

11. The method of claim 7, wherein the recording comprises charting the plurality of ratio measurements.

12. The method of claim 7, further comprising modifying at least a second one of the at least two exercise sessions, relative to a first one of the at least two exercise sessions, based on the indication of anaerobic exercise during the first one of the at least two exercise sessions.

13. The method of claim 7, further comprising modifying a further training period, relative to the training period, based on the indication of effectiveness or ineffectiveness of the training period.

14. The method of claim 8, wherein the bicarbonate salt is sodium bicarbonate.

* * * * *